(12) United States Patent
Fisker et al.

(10) Patent No.: US 11,045,293 B2
(45) Date of Patent: Jun. 29, 2021

(54) METHOD FOR APPLYING DESIGN GUIDES

(71) Applicant: 3SHAPE A/S, Copenhagen (DK)

(72) Inventors: Rune Fisker, Virum (DK); Danni Liljekrans, Copenhagen (DK); Kristoffer Rath Petersen, Frederiksberg (DK)

(73) Assignee: 3Shape A/S, Kobenhavn K (DK)

( * ) Notice: Subject to any disclaimer, the term of this patent is extended or adjusted under 35 U.S.C. 154(b) by 0 days.

(21) Appl. No.: 15/032,503

(22) PCT Filed: Oct. 27, 2014

(86) PCT No.: PCT/EP2014/073008
§ 371 (c)(1),
(2) Date: Apr. 27, 2016

(87) PCT Pub. No.: WO2015/063032
PCT Pub. Date: May 7, 2015

(65) Prior Publication Data
US 2016/0250006 A1   Sep. 1, 2016

(30) Foreign Application Priority Data
Oct. 28, 2013  (DK) .......................... PA 2013 70626

(51) Int. Cl.
*A61C 13/34*   (2006.01)
*A61C 9/00*   (2006.01)
(Continued)

(52) U.S. Cl.
CPC ............... *A61C 13/34* (2013.01); *A61B 1/24* (2013.01); *A61C 9/0046* (2013.01);
(Continued)

(58) Field of Classification Search
CPC . A61C 13/0004; A61C 9/0046; A61C 9/0053; A61C 13/34; G06K 9/00208; G06K 9/00221; G06K 2209/05; A61B 1/24
(Continued)

(56) References Cited

U.S. PATENT DOCUMENTS

| 2004/0029068 A1 | 2/2004 | Sachdeva et al. |
| 2007/0055401 A1* | 3/2007 | Van Bael ............ G06F 3/04845 |
| | | 700/98 |

(Continued)

FOREIGN PATENT DOCUMENTS

| DK | WO 2012000511 A1 * | 1/2012 | ......... A61C 13/0004 |
| WO | 2007019709 | 2/2007 | |

(Continued)

OTHER PUBLICATIONS

International Search Report (PCT/ISA/210) dated Jan. 22, 2015, by the Japanese Patent Office as the International Searching Authority for International Application No. PCT/EP2014/073008.
(Continued)

*Primary Examiner* — King Y Poon
*Assistant Examiner* — Vincent Peren
(74) *Attorney, Agent, or Firm* — Buchanan Ingersoll & Rooney PC

(57) ABSTRACT

A method for placing and using design guides in a virtual environment for use in dental treatment includes steps of obtaining a 3D representation of a dental setup a patient, obtaining a 2D image of at least a part of the face of the patient, aligning the 2D image and the 3D representation, generating at least one design guide based on facial features in the 2D image, and applying the at least one design guide to the 3D representation.

13 Claims, 1 Drawing Sheet

(51) Int. Cl.
  *G06K 9/00* (2006.01)
  *A61C 13/00* (2006.01)
  *A61B 1/24* (2006.01)

(52) U.S. Cl.
  CPC ........ *A61C 9/0053* (2013.01); *A61C 13/0004* (2013.01); *G06K 9/00208* (2013.01); *G06K 9/00221* (2013.01); *G06K 2209/05* (2013.01)

(58) Field of Classification Search
  USPC .......................................................... 345/419
  See application file for complete search history.

(56) References Cited

U.S. PATENT DOCUMENTS

| | | | | |
|---|---|---|---|---|
| 2007/0099147 | A1* | 5/2007 | Sachdeva | A61C 9/0046 433/24 |
| 2007/0276214 | A1* | 11/2007 | Dachille | G06F 19/321 600/407 |
| 2008/0145811 | A1 | 6/2008 | Diers et al. | |
| 2010/0145898 | A1* | 6/2010 | Malfliet | G06T 7/0012 706/47 |
| 2010/0177186 | A1* | 7/2010 | Baranton | G02C 13/003 348/78 |
| 2010/0260383 | A1* | 10/2010 | Truyen | G06T 19/00 382/106 |
| 2011/0276159 | A1* | 11/2011 | Chun | B33Y 50/00 700/98 |
| 2012/0010533 | A1* | 1/2012 | Arnett | A61B 5/0064 600/590 |
| 2012/0015316 | A1 | 1/2012 | Sachdeva et al. | |
| 2012/0010681 | A1 | 5/2012 | Stone-Collonge et al. | |
| 2013/0158958 | A1* | 6/2013 | Methot | A61C 5/77 703/1 |
| 2013/0166312 | A1 | 6/2013 | Lauciello et al. | |
| 2013/0218530 | A1* | 8/2013 | Deichmann | A61C 13/0004 703/1 |
| 2013/0314668 | A1* | 11/2013 | Haddadi | A61B 3/111 351/204 |
| 2014/0313304 | A1 | 10/2014 | Adriaens | |
| 2015/0132718 | A1* | 5/2015 | Kerschensteiner | A61C 13/082 433/196 |

FOREIGN PATENT DOCUMENTS

| | | |
|---|---|---|
| WO | WO 2008/128700 A1 | 10/2008 |
| WO | 2012006717 | 1/2012 |
| WO | WO 2012/000511 A1 | 1/2012 |
| WO | WO 2013/067606 A2 | 5/2013 |

OTHER PUBLICATIONS

Written Opinion (PCT/ISA/237) dated Jan. 22, 2015, by the Japanese Patent Office as the International Searching Authority for International Application No. PCT/EP2014/073008.
Search Report issued in corresponding Danish Patent Application No. PA 2013-70626, dated May 26, 2014. (8 pages).
Daniel Grest, "Marker-Free Human Motion Capture in Dynamic Cluttered Environments from a Single View-Point", zur Erlangung des akademischen Grade, Doktor der Ingenieurwissenschafter (Dr.-Ing.), der Technischen Fakultat der Christian-Albrechts-Universitate zu Kiel, Germany, Dec. 14, 2007 (pp. 1-171).
Communication issued in corresponding European Patent Application No. 14 790 071.6-1126, dated Mar. 23, 2020. (6 pages).

* cited by examiner

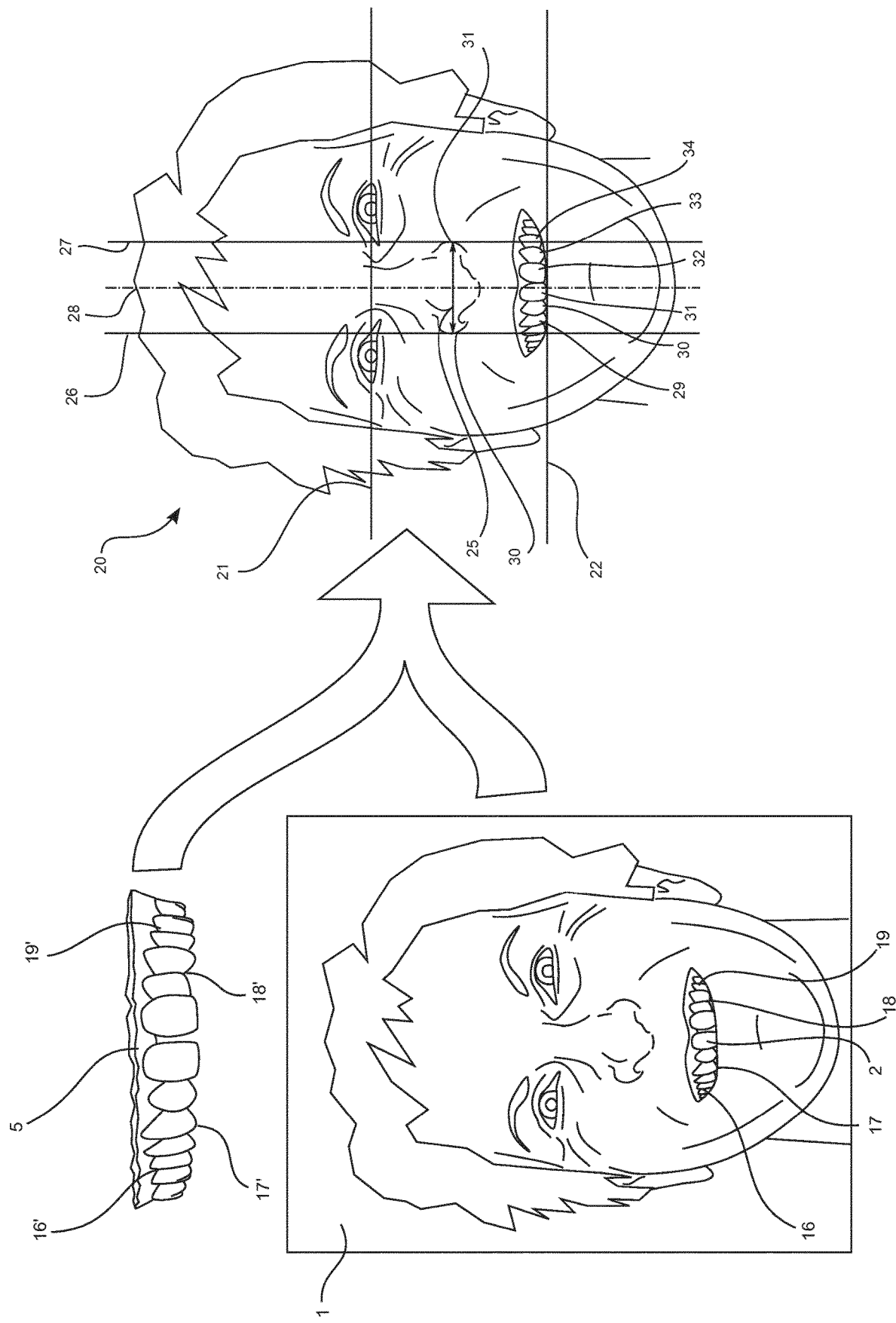

METHOD FOR APPLYING DESIGN GUIDES

FIELD OF THE INVENTION

This invention generally relates to a method for placing and using design guides in a digital environment for use in designing a dental restoration. Placing guidelines properly is advantageous for designing dental restorations which are aesthetic and functional.

BACKGROUND OF THE INVENTION

When providing a restoration or other dental restorative work it is important to obtain a result which is functional as well as aesthetic. Accordingly, a lot has been written and said on how such results are achieved, which results in many types of design rules and guides. For most parts such rules relates to the face and it symmetry.

Examples on such rules are that the smile should be parallel to a line drawn between the pupils of the eyes, or that the canines should follow lines extending from the alar sidewall of the nose.

It has however been difficult to verify such rules during the restorative work and it has only been possible to actually verify the result when the work was done. This is mainly due to the fact that it in manual processes it is difficult to verify whether a design of dental model and the restoration(s) arranged thereon would actually fit the face and facial features of the patient as there has been no easy ways to overlay this information with the face of the patient.

Recently 3D face scanners have been used to scan a face in 3D and overlay this with the 3D dental setup of the restorative work. However, such face scanners are expensive and bulky whereby it is rarely economically viable for a dentist to acquire one.

In order to provide a more economically solution attempts to use 2D images wrapped around a standard 3D model of a face has been used. However, since a standard model is used and the 2D image is warped to fit this standard model this solution only provides a visual presentation and cannot be used to establish design guide.

Accordingly, there is a need for an inexpensive and efficient system and method for establishing design guides for use in designing dental restorations.

SUMMARY

Disclosed is a method for placing and using design guides in a digital environment for use in dental treatment, wherein the method comprises steps of
  obtaining a digital 3D representation of a dental setup of a patient,
  obtaining a digital 2D image of at least a part of the face of the patient,
  aligning the digital 2D image to the digital 3D representation,
  generating at least one design guide based on at least one facial features in the digital 2D image, and
  applying the at least one design guide to the digital 3D representation.

This provides method wherein design guides may be used with high accuracy for dental treatment. The dental treatment can for example be designing a dental restoration. Accordingly, the dental treatment comprises designing teeth modification.

The digital 3D representation can be obtained by using a 3D scanner, such as a desktop scanner or an intraoral scanner. For example the TRIOS intraoral scanner manufactured by 3Shape A/S can be used.

The digital 2D image may be obtained by using a standard 2D digital camera.

In alternative embodiment the digital 3D representation and the digital 2D image are obtained by loading digital files received from a third party who has obtained the content of the files by suitable means.

It is particularly advantageous that the digital 2D image, the digital 3D representation and design guide(s) are aligned together as this allows for the possibility to show the overlaid features in a common view, which has not been before.

Such alignment can be described in different ways. Typically a transformation is established, e.g. by a transformation matrix, which describes how the digital 3D representation and the digital 2D image relates to each other. In some embodiments the transformation describes how the digital 2D image is correctly placed in the coordinate system of the digital 3D representation as determined by the alignment itself.

It will be described in the following how the actual alignment may be performed.

The common view gives the user a direct understanding of what should be included in the dental treatment, and in particular it gives the user an immediate indication on whether the dental treatment applied fulfills certain design requirements.

During alignment the digital 2D image is preferably scaled to the digital 3D representation. In this way the 2D image is true or close to scale and measurements can be derived therefrom as the digital 3D representation typically will be dimensionally stable. In particular, where the digital 3D representation is obtained by a 3D scanner, such as a desktop scanner or intra-oral scanner, the dimensions and scale of the scanned object is obtained simultaneously and may be included in the digital 3D representation.

Both the digital 2D image and the digital 3D representation can be rotated to correct alignment. Preferably, the digital 2D image is rotated so that the pupils are aligned in plane with the horizon whereby the digital 3D representation is rotated to fit.

For higher accuracy the alignment may also comprise alignment to perspective and camera position of the physical camera that was used to obtain the 2D image. This can for example be done by identifying corresponding points on the digital 2D image and the digital 3D representation. Such corresponding points will typically be identified on teeth visible in the digital 2D image, which will be easily identified in the digital 3D representation.

For example with four corresponding points identified in both the digital 2D image and the digital 3D representation, the software is able to estimate the camera position and field of view used when the digital 2D image was taken. These parameters may then be transferred to the view of the digital 3D representation so that the digital 2D image and the digital 3D representation are viewed from the same camera position and field of view and thus are aligned. The principles hereof are for example described in "Marker-Free Human Motion Capture: Estimation Concepts and Possibilities with Computer Vision Techniques from a Single Camera View Point" by Daniel Grest, published by LAP LAMBERT 15 Academic Publishing (Jul. 22, 2010), ISBM-13:978-3838382227.

With the digital 2D image and the digital 3D representation aligned to the same perspective and/or camera position the digital 2D image and the digital 3D representation may be viewed from the camera position estimated during alignment. This results in a 2D image view wherein the digital 3D representation is presented from the same angle, perspective and position in which the digital 2D image was taken, ie. the digital 2D image and the digital 3D representation are visually presented from said same perspective and/or camera position.

This enables the practitioner or other user to use the digital 2D image in the digital design of digital restoration on the digital 3D representation as the result of the esthetics of digital restoration easily can be checked by viewing the result from the 2D image view. Moreover, as discussed in here the 2D image view allows for the practitioner to correctly place design guides on the 2D image while taking the digital 3D representation and any digital designed restoration thereon into consideration.

The design guides can be provided in many different ways. The at least one design guide can for example be a guideline and/or a guide measurement.

In a particular embodiment it is especially advantageous that the method further comprises the following features,
aligning the 2D image and the 3D representation by scaling the 2D image to the 3D representation,
aligning the 2D image and the 3D representation to the same perspective and/or camera position, and
generating the at least design guide as a guide measurement.

This provides a 2D image that is very close to true scale and enables the user to do measurements with the guide measurement on the 2D image that are reliable. Such measurements can for example be used to determine teeth designs or selecting pre-designed teeth from a teeth library.

Aligning the digital 2D image and the digital 3D representation to the same perspective and/or camera position can be done as described above. For example by identifying corresponding point or areas on the teeth visible in the digital 2D image and identifiable in the digital 3D representation.

The method can for example comprise generating a guideline, which for example is used in determining an occlusal plane of the digital 3D representation based on an inter-pupillary guideline extending between the pupils of the patient.

The occlusal plane can subsequently be used when designing the teeth. For example, at least one digital restoration representing an incisor of the patient can be manipulated so to contact the occlusal plane of the digital 3D representation.

In another embodiment the method comprises determining a design guide which is at least one canine guideline extending from the alar sidewall of the nose in the digital 2D image. This advantageously facilitate designing canines, e.g. by manipulating at least one digital restoration representing a canine so to extend along a canine guideline.

In yet another embodiment, the method comprises determining a midline extending down the center of the face equidistant between the pupils of the eyes. The midline can advantageously be used as a design guide where the restorations representing the upper central incisors are manipulated so the they extend on opposite sides of the midline.

In another embodiment the method further comprises determining a nose guide measurement as the nose width from the digital 2D image. This is preferably done after the 2D image has been aligned to the 3D representation, whereby the measurement will be 1:1.

Such nose guide measurement can for example aid the dental technician to choose dimensions of the incisor or pick a suitable set of library teeth from a digital design library. The set of library teeth can serve as basis for a digital restoration template from which the digital restoration can be generated.

In a second aspect there is disclosed a method for placing and using design guides in a digital environment for use in dental treatment, wherein the method comprises steps of
obtaining a digital 3D representation of a dental setup of a patient,
obtaining a digital 2D image of at least a part of the face of the patient,
aligning the digital 2D image to the digital 3D representation by scaling the 2D image to the 3D representation, and
generating at least one design measurement based on facial features in the digital 2D image.

As described above the scaling of the digital 2D image to the digital 3D representation results in a digital 2D image which is close to scale. Thus, the digital 2D image may be used for basis for measurements. Such measurement can be used for different design choices, for example, selecting specific pre-designed teeth from a teeth design library.

In one embodiment the method comprises aligning the 2D image and the 3D representation to the same perspective and/or camera position. Preferably the digital 2D image and the digital 3D representation are visually presented from said same perspective and/or camera position.

In another embodiment of the second aspect the digital 2D image is rotated relative to the digital 3D image, In yet a further embodiment the method comprises determining a nose guide measurement as the nose width from the digital 2D image. The nose width can for example be used as basis for selecting pre-designed teeth from a design library.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 1 shows an embodiment of the invention wherein design guides are applied to the digital 2D image and used in designing digital 3D dental restorations.

DETAILED DESCRIPTION

In the following description, reference is made to the accompanying FIGURE, which show by way of illustration how the invention may be practiced.

In one embodiment as shown in FIG. 1, a 2D image 1 of the face of a patient is obtained. The 2D image shows at least a part of the teeth 2. The 2D image was obtained as a digital 2D image by using a standard digital camera.

A 3D representation 5 of the patient's dental setup is also obtained. The 3D representation was obtained as digital 3D representation by scanning the teeth of the patient by using an intra-oral scanner, such as the TRIOS manufactured by 3Shape A/S. Using the TRIOS also provides a 3D representation which is very accurate and for all purposes in the current disclosure true to scale.

The 2D image 1 and the 3D representation are aligned to each other. This is done by identifying four reference points 16, 17, 18, 19 on the visible teeth in the 2D image and corresponding four reference points 16', 17', 18', 19' on the teeth on the 3D representation. Based on the four reference points it is possible to align the 2D image and the 3D representation in scale, position and perspective. In other words the 2D image and the 3D representation are aligned so that they are viewed from the camera position as the 2D image was taken in, As mentioned earlier the principles applied to do this are described in "Marker-Free Human Motion Capture: Estimation Concepts and Possibilities with Computer Vision Techniques from a Single Camera View Point" by Daniel Grest, published by LAP LAMBERT Academic Publishing (Jul. 22, 2010), ISBM-13:978-3838382227.

With the 2D image and the 3D representation aligned the teeth of the 3D representation are made visible on the 2D image. This can be done in several ways.

In one way the 2D image is placed in front of the 3D representation and the teeth in the 2D image are cut out. This makes the 3D representation visible through the cut-out area.

In another way the teeth of the 3D representation are overlaid onto the 2D image.

All the teeth can be shown or only selected teeth are shown. In the current case restorations 30, 31, 32 and 33 of the incisors are shown. The restorations have previously been designed using general known methods and tool within dental CAD design environments, such as the Dental System software by 3Shape A/S. Since the design software uses the 3D representation 5 as basis for the restorations designs, the restorations automatically becomes aligned with the 3D representation. Accordingly, as the 3D representation is aligned with 2D image the designed restorations are also aligned.

With the 2D image and the 3D representation aligned, design guides can be applied to the 2D image as shown in the aligned view 20. The aligned view 20 shows the aligned 2D image and 3D representation from the 2D image view which corresponds to the camera view of the physical camera used to take the 2D image.

An intra-pupillary guideline 21 is established by generating a line between the pupils of the eye. Based on the intra-pupillary guideline 21 the occlusive plane 22 can established as this is often estimated to be parallel with the intra-pupillary guideline 21. The dental technician can then use the occlusal plane as a guide when designing restorations or setting up a denture. For example he may ensure that the frontal incisors 31 and 32 touch the occlusal plane 22.

Another design guide is provided by the nose guide measurement 25, which is width of the nose—i.e. the distance between the alar sidewalls 30,31 of the nose. This measurement is often used a basis for choosing teeth from a design library.

Furthermore there are established canine guidelines 26, 27 which extend from the alar sidewalls 30,31 of the nose in parallel with the midline 28 of the face. The canine guidelines are used by the dental technician to indicate where the canines should be placed. In the current case the left canine 34 follows the canine guideline 27, however, the right canine 29 does not follow the right canine guideline 26. Accordingly, in order to establish a more esthetic and symmetrical smile the dental technician may consider providing additional restorative work on the right side of the patient.

The guidelines are then applied by the dental technician when designing dental restoration on the 3D representation.

The guidelines can be maintained in the 2D image so that when the dental technician has made changes to the design he can change the view back to the frontal view where the 2D image is aligned with the 3D representation to check the design against the 2D image and the guidelines.

Alternatively the guidelines, for example guidelines 26, 27, may be extruded into guide planes so that the dental technician always has a reference no matter which angle or view the 3D representation is placed in. The guide planes may be extruded perpendicular to the aligned view of the 2D image and the 3D representation, or an angle may be chosen by the dental technician at which the extrusion occurs, and/or the dental technician may identify one or more points which should be include in the guide plane.

As can be understood the dental technician may design the digital dental restoration simultaneously as watching the result on the aligned 2D image and 3D representation. This can for example be done by having a window open wherein the 2D image and the 3D image is viewed aligned together from the camera position wherein the 2D image was taken. In another window changes are done to the digital dental restoration placed on the 3D representation. The changes are continuously updated and shown in the aligned view and the technician can thereby instantly see if the changes are useful.

In addition the design guides can be used as threshold, ie. They prevent a design from passing or come within preset boundaries of that threshold. In other situations a snap ability can be employed wherein design are snapped to the guidelines.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for placing and using design guides in a digital environment for use in dental treatment of a patient having dentition and a face, wherein the method comprises steps of obtaining a digital 3D representation of the patient's dentition, obtaining a digital 2D image of at least a part of the face of the patient, aligning the digital 2D image with the digital 3D representation, generating at least one guide line based on at least one facial feature outside of the mouth in the digital 2D image, generating a guide plane in the digital 3D representation by extruding the guide plane from the guide line, and rotating the digital 2D image so that pupils on the face of the patient are aligned with the horizon.

2. A method according to claim 1, wherein the alignment of the digital 2D image and the digital 3D representation comprises scaling the digital 2D image to the digital 3D representation.

3. A method according to claim 1, wherein the digital 2D image and the digital 3D representation are aligned to a same perspective or camera position.

4. A method according to claim 3, wherein the digital 2D image and the digital 3D representation are visually presented from said same perspective or camera position.

5. A method according to claim 1, wherein the at least one facial feature comprises two pupils of the patient and the method further comprises determining an occlusal plane of the digital 3D representation based on an inter-pupillary guideline extending between the pupils of the patient.

6. A method according to claim 5, wherein the method further comprises manipulating at least one digital restoration representing an incisor of the patient to contact the occlusal plane of the digital 3D representation.

7. A method according to claim 1, wherein the at least one facial feature is an alar sidewall of the patient and the method further comprises determining at least one canine guideline extending from the alar sidewall of a nose in the digital 2D image.

8. A method according to claim 7, wherein the method further comprises manipulating at least one digital restoration representing a canine so to extend along the canine guideline.

9. A method according to claim 1, wherein the method further comprises determining a midline extending down a center of the face equidistant between pupils of the eyes.

10. A method according to claim 9, wherein the method further comprises manipulating digital restorations representing upper central incisors so that they extend on opposite sides of the midline.

11. A method according to claim 1, wherein the guide plane is extruded perpendicular to an aligned view of the 2D image and the 3D representation.

12. A method according to claim 1, further comprising the steps of
identifying at least one point on the 2D image and the 3D representation, and
extruding the guide plane so that the at least one point is included in the guide plane.

13. A method according to claim 1, wherein the at least one facial feature is one of the pupils, a nose of the patient, and an alar sidewall of the patient.

* * * * *